United States Patent [19]

Miyata et al.

[11] Patent Number: 5,376,665

[45] Date of Patent: Dec. 27, 1994

[54] PHOSPHONIC DIESTER DERIVATIVES

[75] Inventors: Kazuyoshi Miyata; Yasuo Shoji; Yoshihiko Tsuda, all of Naruto; Kazuhiko Tsutsumi, Tokushima; Yasuhide Inoue, Naruto; Chieko Naba, Naruto; Yasuhisa Kurogi, Naruto, all of Japan

[73] Assignee: Otsuka Pharmaceutical Factory, Inc., Tokushima, Japan

[21] Appl. No.: 182,145

[22] PCT Filed: May 20, 1993

[86] PCT No.: PCT/JP93/00660

§ 371 Date: Jan. 14, 1994

§ 102(e) Date: Jan. 14, 1994

[87] PCT Pub. No.: WO93/23409

PCT Pub. Date: Nov. 25, 1993

[30] Foreign Application Priority Data

May 21, 1992 [JP] Japan .................................. 4-128711

[51] Int. Cl.⁵ ................. C07D 235/04; C07D 221/04; A61K 31/415; A61K 31/44
[52] U.S. Cl. ..................................... 514/301; 514/302; 514/303; 514/367; 514/375; 514/395; 546/23; 548/113
[58] Field of Search .................. 548/113; 546/23; 514/367, 375, 395, 301, 302, 303

[56] References Cited

FOREIGN PATENT DOCUMENTS 2500744  3/1990  Japan .................................. 548/113

OTHER PUBLICATIONS

CA 117(19):192072d Preparation . . . acids, Fujita et al., p. 826, 1992.
28–Heterocycles, vol. 110, 198, pp. 692–693, 110: 57664p, "(Pyridinylmethyl)sulfinylbenzimidazole derivatives as antiulcer agents, their preparation and formulations containing them", 1986.

*Primary Examiner*—Mary C. Lee
*Assistant Examiner*—Joseph K. McKane
*Attorney, Agent, or Firm*—Sughrue, Mion, Zinn, Macpeak & Seas

[57] ABSTRACT

The invention provides a phosphonic diester derivative of the general formula

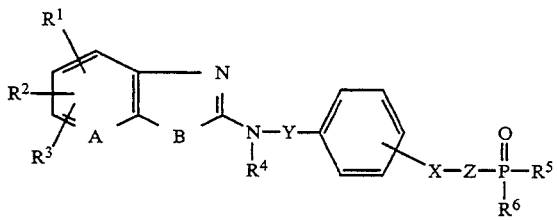

The phosphonic diester derivative of the invention has hypoglycemic and hypolipidemic activities, for instance, and is of value as an antidiabetic or anti-hyperlipidemic agent.

10 Claims, No Drawings

PHOSPHONIC DIESTER DERIVATIVES

TECHNICAL FIELD

The present invention relates to novel phosphonic diester derivatives.

PRIOR ART

The phosphonic diester derivatives of the invention are novel compounds not heretofore described in the literature.

DISCLOSURE OF THE INVENTION

The object of the invention is to provide compounds of value as medicines as will be described hereinafter.

The present invention provides a phosphonic diester derivative of the following general formula (1):

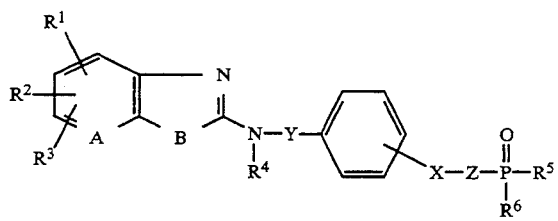

[wherein $R^1$, $R^2$ and $R^3$ are the same or different and each represents a hydrogen atom, a lower alkyl group, a phenyl group, a lower alkoxy group, a halogen-substituted lower alkyl group, a halogen-substituted lower alkoxy group, a lower alkanoyl group, a benzoyl group, a (lower)alkoxycarbonyl group, a nitro group, a halogen atom, a (lower)alkylthio group, a phenyl(lower)alkoxy group, a carbamoyl group or a (lower)alkoxycarbonyl(lower)alkoxy group; $R^4$ represents a hydrogen atom, a lower alkyl group or a phenyl(lower) alkyl group; $R^5$ and $R^6$ are the same or different and each represents a lower alkoxy group, a phenyl group, a phenoxy group, a phenyl(lower)alkoxy group or a hydroxyl group; A represents a carbon atom or a nitrogen atom; B represents a group of the formula $=NR^7$ (where $R^7$ represents a hydrogen atom, a lower alkyl group or a phenyl(lower)alkyl group), an oxygen atom or a sulfur atom; Y represents a group of the formula $C=O$ or a group of $SO_2$; X represents an oxygen atom or a bond; Z represents a lower alkylene group optionally having a lower alkyl or phenyl(lower)alkyl group as a substituent or a bond; provided, however, that X and Z do not concurrently represent bonds]

Each of the groups relevant to the above general formula (1) includes the following exemplary species.

The lower alkyl group includes straight- or branched-chain lower alkyl groups such as methyl, ethyl, propyl, isopropyl, butyl, isobutyl, tert-butyl, pentyl, hexyl and so on.

The lower alkoxy group includes methoxy, ethoxy, propoxy, isopropoxy, butoxy, pentyloxy, hexyloxy and so on.

The halogen-substituted lower alkyl group includes trifluoromethyl, pentafluoroethyl, heptafluoropropyl, nonafluorobutyl, undecafluoropentyl, tridecafluorohexyl and so on.

The halogen-substituted lower alkoxy group includes trifluoromethoxy, pentafluoroethoxy, heptafluoropropoxy, nonafluorobutoxy, undecafluoropentyloxy, tridecafluorohexyloxy and so on.

The lower alkanoyl group includes acetyl, propionyl, butyryl, valeryl, pivaloyl, hexanoyl, heptanoyl and so on.

The lower alkoxycarbonyl group includes methoxycarbonyl, ethoxycarbonyl, propoxycarbonyl, butoxycarbonyl, pentyloxycarbonyl, hexyloxycarbonyl and so on.

The phenyl(lower)alkyl group includes benzyl, 2-phenylethyl, 3-phenylpropyl, 4-phenylbutyl, 5-phenylpentyl, 6-phenylhexyl and so on.

The halogen atom includes fluorine, clorine, bromine and iodine.

The lower alkylthio group includes methylthio, ethylthio, propylthio, butylthio, pentylthio, hexylthio and so on.

The phenyl(lower)alkoxy group includes benzyloxy, 2-phenylethoxy, 3-phenylpropoxy, 4-phenylbutoxy, 5-phenylpentyloxy, 6-phenylhexyloxy and so on.

The lower alkoxycarbonyl(lower)alkoxy group includes methoxycarbonylmethoxy, 2-ethoxycarbonylethoxy, 3-ethoxycarbonylpropoxy, 4-ethoxycarbonylbutoxy, 5-ethoxycarbonylpentyloxy, 6-ethoxycarbonylhexyloxy, 2-butoxycarbonylethoxy, hexyloxycarbonylmethoxy and so on.

The lower alkylene group optionally having a lower alkyl or phenyl(lower)alkyl group as a substituent includes methylene, ethylene, trimethylene, tetramethylene, pentamethylene, hexamethylene, ethylidene, propylidene, butylidene, pentylidene, hexylidene, heptylidene, 2-phenylethylidene, 3-phenylpropylidene, 4-phenylbutylidene, 5-phenylpentylidene, 6-phenylhexylidene, 7-phenylheptylidene and so on.

The phosphonic diester derivative of general formula (1) according to the present invention has excellent hypolipidemic and hypoglycemic activities and is, therefore, useful for the treatment and prevention of various types of hyperlipidemic diseases such as hypercholesterolemia, hypertriglyceridemia, hyperphospholipidemia, hyper-free fatty acidemia, etc. and diabetes. Moreover, the phosphonic diester derivative of the invention not only produces therapeutic and prophylactic effects on cataract but has hypotensive activity as well and is, therefore, of value as a therapeutic and prophylactic agent for cataract and hypertension.

The phosphonic diester derivative of general formula (1) according to the invention can be produced by several different processes. Some exemplary processes are schematically shown hereunder.

(Reaction Schema-1)

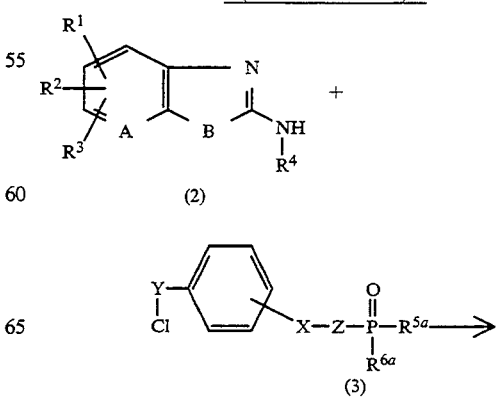

-continued
(Reaction Schema-1)

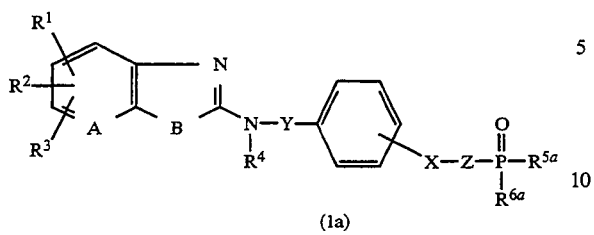

(1a)

[wherein $R^1$, $R^2$, $R^3$, $R^4$, A, B, X, Y and Z are as defined hereinbefore. $R^{5a}$ and $R^{6a}$ are the same or different and each represents a lower alkoxy group, a phenyl group, a phenyl(lower)alkoxy group or a phenoxy group]

According to the process shown in Reaction Schema-1, the objective compound (1a) of the invention can be obtained by reacting compound (2) with acid chloride derivative (3) in the presence of an acid acceptor in an inert solvent. The inert solvent mentioned above includes, among others, aromatic or aliphatic hydrocarbons such as benzene, toluene, xylene, petroleum ether, etc., acylic or cyclic ethers such as diethyl ether, 1,2-dimethoxyethane, tetrahydrofuran (THF), 1,4-dioxane, etc., ketones such as acetone, methyl ethyl ketone, acetophenone, etc., and halogenated hydrocarbons such as dichloromethane, chloroform, carbon tetrachloride, 1,2-dichloroethane and so on. The acid acceptor is preferably a tertiary amine such as triethylamine, N,N-diethylaniline, N-methylmorpholine, pyridine, 4-dimethylaminopyridine and so on. The relative amount of said compound (2) and acid chloride derivative (3) is not particularly critical but the latter is preferably used in an equimolar to excess proportion with respect to the former. Usually, the acid acceptor mentioned above is preferably used in an equimolar or excess proportion relative to said acid chloride derivative (3). This reaction proceeds under cooling, at room temperature or under heating but it is usually advantageous to conduct the reaction within the temperature range of 0° C. to the reflux temperature of the solvent used. Generally the reaction goes to completion in about 0.5 - 10 hours.

(Reaction Schema-2)

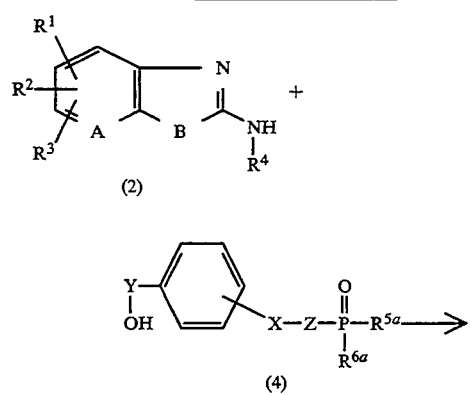

-continued
(Reaction Schema-2)

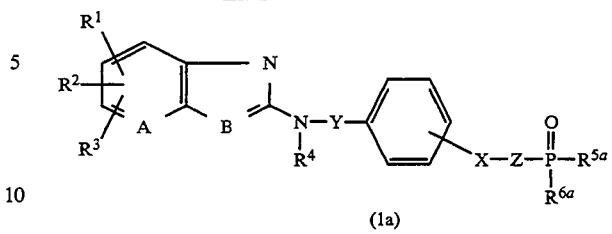

(1a)

[wherein $R^1$, $R^2$, $R^3$, $R^4$, $R^{5a}$, $R^{6a}$, A, B, X, Y and Z are as defined hereinbefore]

According to the process shown in Reaction Schema-2, the objective compound (1a) of the invention can be obtained by reacting compound (2) with compound (4) in the presence of a condensing agent in an inert solvent. The inert solvent which can be used is any of the known aprotic solvents, although N,N-dimethylformamide (DMF) is particularly useful. The condensing agent includes, among others, N,N'-dicyclohexylcarbodiimide (DCC), 1-hydroxybenzotriazole, N-hydroxysuccinimide, diethyl cyanophosphonate, diphenylphosphoryl azide and so on. It is particularly advantageous to employ diethyl cyanophosphonate in combination with triethylamine. The relative amount of compounds (2) and (4) in the above reaction is not critical but can be liberally selected from a broad range. However, it is generally recommendable to use the former compound in an equimolar or excess proportion, preferably an approximately equimolar proportion, relative to the latter compound. The above condensing agent is used in an equimolar to excess proportion, preferably a small excess, relative to compound (4). This reaction is conducted generally under ice-cooling to room temperature for about 0.5-2 hours.

(Reaction Schema-3)

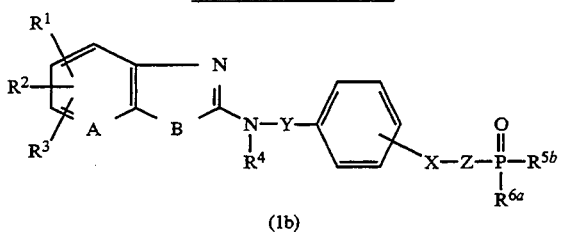

(1b)

↓ Partial hydrolysis

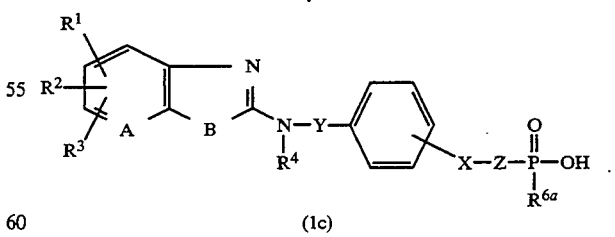

(1c)

[wherein $R^1$, $R^2$, $R^3$, $R^4$, $R^{6a}$, A, B, X, Y and Z are as defined above. $R^{5b}$ represents a lower alkoxy group]

The partial hydrolysis shown in the above Reaction Schema-3 is carried out by reacting compound (1b) with a lithium halide such as lithium bromide, lithium chloride, lithium iodide, etc. and thereafter treating the reaction product with a mineral acid such as hydrochloric acid, sulfuric acid and so on. The above reaction can be carried out in an inert solvent, such as acetonitrile, DMF, etc., using a stoichiometric excess of the lithium halide at room temperature~the reflux temperature of the solvent for 5-24 hours.

Among the starting compounds for the production of the compound of the invention, compounds of the formulas (3') and (4') can be prepared by the processes shown below in Reaction Schema-4.

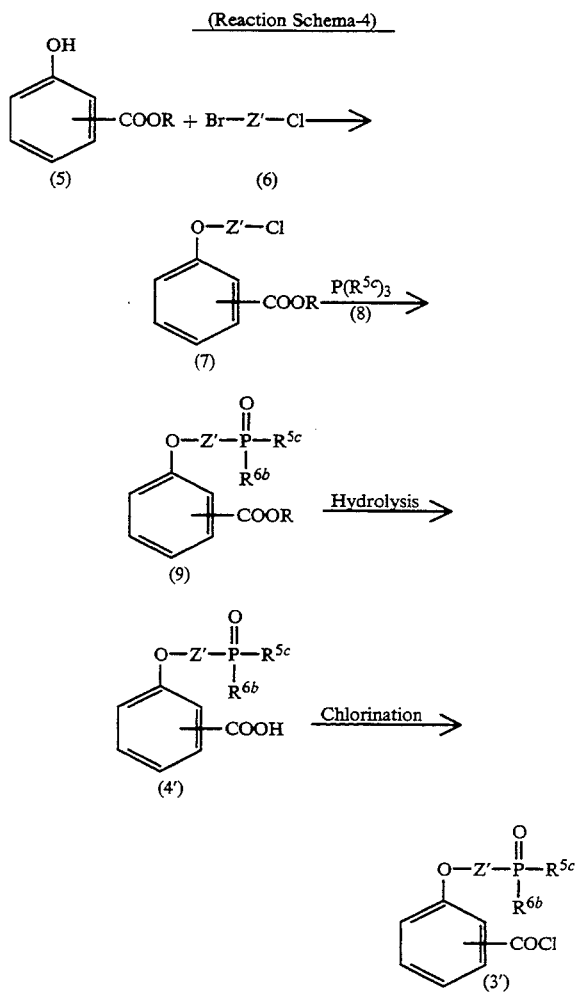

[wherein $R^{5c}$ represents a lower alkoxy group, a phenoxy group or a phenyl(lower)alkoxy group; $R^{6b}$ is identical to $R^{5c}$; Z' represents a lower alkylene group; R represents a lower alkyl group]

Referring to the above schema, the reaction between compound (5) and compound (6) is carried out in the presence of an alkali, such as sodium carbonate, potassium carbonate, sodium hydrogen carbonate, sodium hydroxide, etc., in an inert solvent, such as DMF, N,N-dimethylacetamide (DMA), hexamethylphosphoric triamide (HMPA), acetone, methanol, ethanol, methanol-water, ethanol-water and so on. This reaction goes to completion in about 5-30 hours at room temperature to the reflux temperature of the solvent.

The resultant compound (7) can be reacted with a phosphorous triester (8) to give compound (9). This reaction can be carried out in a solvent such as lower alcohols, aromatic or aliphatic hydrocarbons, DMF, etc. but is preferably conducted in the absence of a solvent in most cases. If necessary, a salt of iodine such as sodium iodide, potassium iodide, etc. can be added to the reaction system and usually the reaction is preferably conducted using said phosphorous triester (8) in excess at a temperature of about 130°-170° C. for about 1-20 hours.

The compound (9) can then be hydrolyzed to compound (4'). This hydrolysis reaction is carried out in the presence of an aqueous alkali solution, such as aqueous sodium hydroxide solution, aqueous potassium hydroxide solution, etc., in an inert solvent such as methanol, ethanol, 2-propanol, etc. and this reaction goes to completion in about 1-15 hours at a temperature somewhere between 0° C. and room temperature.

The compound (4') can be chlorinated at the carboxyl function to give compound (5'). This chlorination reaction is carried out using dichloromethane, chloroform, DMF or the like either singly or in combination as the solvent and a small excess of thionyl chloride, phosphorus oxychloride, phosphorus pentachloride or the like as the chlorinating agent at room temperature to about 60° C. for about 1-8 hours.

The product compound in each of the above processes can be easily isolated and purified by the conventional separation procedures. Such procedures include adsorption chromatography, preparative thin-layer chromatography, solvent extraction, recrystallization and so on.

Among the species of compound (I) according to the invention, the compound in which Z is a lower alkylene group having a lower alkyl or phenyl(lower)alkyl group as a substituent may exist as optical isomers which, of course, are subsumed in the concept of the compound of the invention. The above optical isomers can be easily fractionated by the conventional resolution procedures such as optical resolution.

The compound of the invention is put to use in a variety of pharmaceutical compositions prepared using suitable pharmaceutically acceptable carriers. Such pharmaceutically acceptable carriers include various diluents or excipients such as fillers, volume builders, binders, humectants, disintegrators, surfactants, lubricants, etc. and are selectively employed according to the desired dosage form.

The above pharmaceutical composition can be provided in a variety of unit dosage forms according to the intended medical treatment. Typical examples are tablets, pills, powders, solutions, suspensions, emulsions, granules, capsules, suppositories, injections (solutions, suspensions, etc.) and eye-drops.

The molding of tablets can be made using, as said pharmaceutically acceptable carriers, an excipient such as lactose, sucrose, sodium chloride, glucose, urea, starch, calcium carbonate, kaolin, crystalline cellulose, silicic acid, potassium phosphate, etc., a binder such as water, ethanol, propanol, simple syrup, glucose syrup, starch solution, gelatin solution, carboxymethylcellulose, hydroxypropylcellulose, methylcellulose, polyvinylpyrrolidone, etc., a disintegrator such as carboxymethylcellulose sodium, carboxymethylcellulose calcium, low-substituted hydroxypropylcellulose, dry starch, sodium alginate, agar powder, laminaran powder, sodium hydrogen carbonate, calcium carbonate, etc., a surfactant such as polyoxyethylene sorbitan fatty acid ester, sodium lauryl sulfate, stearyl monoglyceride, etc., a disintegration inhibitor such as sucrose, stearin, cacao butter, hydrogenated oil, etc., an absorption promoter such as quaternary ammonium bases, sodium lauryl sulfate, etc., a humectant such as glycerin, starch, etc., an adsorbent such as starch, lactose, kaolin, bentonite, colloidal silica, etc., and a lubricant such as purified talc, salts of stearic acid, boric acid powder, polyethylene glycol and so on. Furthermore, such tablets can be coated, if necessary, to provide sugar-coated tablets, gelatin-coated tablets, enteric tablets, film-coated tablets, etc. or be processed into double-layer or multiple-layer tablets.

In the manufacture of pills, various excipients such as glucose, lactose, starch, cacao butter, hydrogenated vegetable oil, kaolin, talc, etc., binders such as gum arabic powder, gum tragacanth powder, gelatin, ethanol, etc. and disintegrators such as laminaran, starch, etc. can be employed.

The capsules can be manufactured in the conventional manner by blending the compound of the invention with any of the various pharmaceutically acceptable carriers mentioned above and filling the resulting composition into hard gelatin capsule shells, soft gelatin capsule shells or the like.

The suppositories can be manufactured using polyethylene glycol, cacao butter, higher alcohols or their esters, gelatin, semisynthetic glycerides, etc. as the carrier.

When the compound of the invention is to be provided in an injectable form such as a solution, emulsion or suspension, the preparation is preferably sterilized and rendered isotonic with respect to the blood. As the diluent for use in such a preparation, water, ethyl alcohol, macrogols, propylene glycol, ethoxylated isostearyl alcohol, polyoxy-isostearyl alcohol, polyoxyethylene sorbitan fatty acid esters, etc. can be employed. In this operation, sodium chloride, glucose or glycerin may be added to the composition in a sufficient amount to provide an isotonic solution and the conventional solubilizer, buffer and local anesthetic can also be added.

The eye-drops can be manufactured in the conventional manner using sterile distilled water as the vehicle, sodium dihydrogen phosphate and/or sodium monohydrogen phosphate, for instance, as the buffer, sodium chloride or the like as the isotonizing agent, and benzalkonium chloride, chlorobutanol or the like as the antimicrobial agent.

If necessary, various coloring agents, preservatives, perfumes, flavors, sweeteners etc. as well as other pharmacologically active substances can be incorporated in the various dosage forms mentioned above.

There is no particular limitation on the treatment regimen for the pharmaceutical composition of the invention. Thus, the proper regimen can be determined according to the particular dosage form, patient's age, sex and other characteristics, severity of disease and other conditions. For example, said tablets, pills, solutions, suspensions, emulsions, granules and capsules are administered by the oral route. The injections are administered either as they are or in admixture with the conventional glucose, amino acid or other infusions by the intravenous route or, if necessary, alone by the intramuscular, intradermal, subcutaneous or intraperitoneal route. The suppositories are administered intrarectally and the eye-drops are instilled into the eye.

The proportion of the compound of the invention in the pharmaceutical composition described above is not much critical and can be liberally selected from a broad range. Generally, however, it is advantageous to insure that the compound accounts for about 1 to 70 weight % of the final composition. The dosing amount of the pharmaceutical composition can be selected according to the selected regimen, patient's age, sex and other characteristics, severity of disease and other conditions. Generally, however, the dosage of the compound of the invention as the active ingredient is preferably about 0.5–20 mg per kg body weight and this amount can be administered in 1~4 divided doses. In the case of an ophthalmic preparation for topical application, the dosage of the active compound is preferably selected from the range of about 0.3–2 $\mu$g.

BEST MODE FOR PRACTICING THE INVENTION

The following production examples for the compound of the invention, formulation examples for pharmaceutical compositions using the compound of the invention and pharmacological test examples are intended to describe the invention in further detail.

EXAMPLE 1

Production of diethyl 4-[(2-benzothiazolyl)carbamoyl]benzylphosphonate

In 30 ml of dry dichloromethane were dissolved 3.0 g of 2-aminobenzothiazole and 10 ml of pyridine and while the resulting solution was stirred under ice-cooling, a solution of 5.8 g 4-[(diethoxyphosphoryl)methyl]-benzoyl chloride in 10 ml dry dichloromethane was slowly added dropwise. The stirring was continued at room temperature for 10 hours, after which the reaction mixture was diluted with 30 ml of 10% aqueous sodium hydrogen carbonate solution and extracted with chloroform. The chloroform layer was washed serially with 30 ml of 10% hydrochloric acid and 30 ml of water and dried over anhydrous sodium sulfate and the solvent was distilled off under reduced pressure. The residue was subjected to silica gel column chromatography (eluent: chloroform-ethyl acetate=1:1) and the resulting crude crystals were recrystallized from ethanol to provide 6.8 g of the title compound as colorless crystals. The structure and melting point of the compound thus obtained are shown in Table 1.

EXAMPLE 2–26

Various species of the compound of the invention were obtained in the same manner as Example 1. The structures and melting points of these compounds are also shown in Table 1.

EXAMPLE 27–45

Various species of the compound of the invention were produced in the same manner as Example 1. The structures and melting points of these compounds are shown in Table 2. As to an oily compound, its $^1$H—NMR spectrum and mass spectrum (MS) are also shown in the table.

EXAMPLE 46

Production of ethyl 4-[(4-methoxybenzothiazol-2-yl)-carbamoyl]benzylphosphonate

In 50 ml of dry acetonitrile were suspended 5.2 g (12 mM) of the compound obtained in Example 3 and 5.2 g (60 mM) of lithium bromide and the suspension was refluxed for 20 hours. The reaction mixture was then allowed to cool to room temperature and the resultant precipitate was recovered by filtration and washed with three 60 ml portions of acetonitrile. The crystals thus obtained were dissolved in 400 ml of water and while the solution was stirred at room temperature, 10 ml of concentrated hydrochloric acid was gradually added. The mixture was stirred at room temperature for 30 minutes, at the end of which time the resultant crystals were recovered by filtration and washed with three 300 ml portions of water. The crude crystals thus obtained were suspended in 200 ml of hot methanol and the insolubles were collected by filtration and washed with 50 ml of methanol. The resultant crystals were further suspended in 200 ml of methanol-chloroform (1:1) and the insolubles were recovered by filtration and washed with 50 ml of methanol and 50 ml of chloroform in the order mentioned to provide 1.8 g of the title compound as colorless crystals. The structure and melting point of this compound are shown in Table 2.

EXAMPLE 47

Production of diethyl 2-[4-{(4-methoxybenzothiazol-2-yl)carbamoyl}phenoxy]ethylphosphonate To 300 ml of acetonitrile were added 16.6 g (0.1 mole) of ethyl 4-hydroxybenzoate, 31.6 g (0.22 mole) of 1-bromo-2-chloroethane and 60.8 g of anhydrous potassium carbonate and the mixture was refluxed for 20 hours. The reaction mixture was then allowed to cool to room temperature and the solid matter was filtered off. The filtrate was concentrated under reduced pressure. To the resultant oily residue were added 15 g (0.1 mole) of sodium iodide and 50 g (0.3 mole) of triethyl phosphite and the mixture was stirred at 160° C. for 18 hours. The reaction mixture was then allowed to cool to room temperature, after which 50 ml of ethanol was added to the reaction mixture. While this mixture was stirred under ice-cooling, 100 ml of 2N aqueous sodium hydroxide solution was gradually added portionwise. The mixture was stirred at room temperature for 12 hours, at the end of which time 150 ml of water and 150 ml of chloroform were added. After phase separation, the water layer was separated. This aqueous solution was acidified with 150 ml of 4N hydrochloric acid and extracted with chloroform. The chloroform layer was washed with 200 ml of water, dried over anhydrous sodium sulfate and concentrated under reduced pressure. The residue was purified by silica gel column chromatography (eluent: chloroform-ethyl acetate=1:1) to provide 3.3 g of 4-[2-(diethoxyphosphoryl)ethoxy]benzoic acid as colorless crystals (m.p. 86°–88° C.).

Then, 3.0 g (10 mM) of the above crystals were suspended in 15 ml of dry dichloromethane and while the suspension was stirred at room temperature, 1.25 g (10.5 mM) of thionyl chloride and 0.22 g (3 mM) of DMF were added. The mixture was further stirred at 40° C. for 1 hour. The resulting reaction mixture was then directly subjected to a reaction similar to that described in Example 1 to provide the title compound.

The structure and melting point of this compound are shown in Table 2.

EXAMPLE 48

Production of diethyl 3-[4-{(4-methoxybenzothiazol-2-yl)carbamoyl}phenoxy]propylphosphonate Using 1-bromo-3-chloropropane, the procedure of Example 47 was otherwise repeated to provide the title compound via 4-[3-(diethoxyphosphoryl)propoxy]benzoic acid (m.p. 107°–110° C.).

The structure and melting point of this compound are shown in Table 2.

TABLE 1

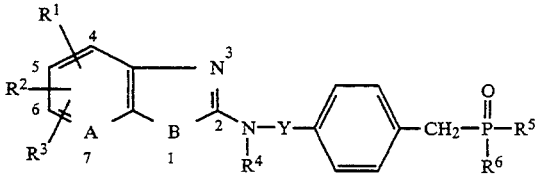

OEt: ethoxy group, Me: methyl group,
OMe: methoxy group, Ph: phenyl group

Example 1
Structure:
$R^1 = R^2 = R^3 = R^4 = H$, $R^5 = R^6 = OEt$, $A = CH$, $B = S$, $Y = C = O$
Mp: 189.5–191° C.
Recrystallization Solvent: Ethanol Example 2
Structure:
$R^1 = 4\text{-Me}$, $R^2 = R^3 = R^4 = H$, $R^5 = R^6 = OEt$,
$A = CH$, $B = S$, $Y = C = O$
Mp: 154–156° C.
Recrystallization Solvent: Chloroform-n-hexane Example 3
Structure:
$R^1 = 4\text{-OMe}$, $R^2 = R^3 = R^4 = H$, $R^5 = R^6 = OEt$,
$A = CH$, $B = S$, $Y = C = O$
Mp: 166–168° C.
Recrystallization Solvent: Ethanol-n-hexane Example 4
Structure:
$R^1 = 4\text{-OCF}_3$, $R^2 = R^3 = R^4 = H$, $R^5 = R^6 = OEt$,
$A = CH$, $B = S$, $Y = C = O$
Mp: 227–228° C.
Recrystallization Solvent: Ethanol Example 5
Structure:
$R^1 = 4\text{-Cl}$, $R^2 = R^3 = R^4 = H$, $R^5 = R^6 = OEt$,
$A = CH$, $B = S$, $Y = C = O$
Mp: 183–184.5° C.
Recrystallization Solvent: Chloroform-n-hexane Example 6
Structure:
$R^1 = 6\text{-Me}$, $R^2 = R^3 = R^4 = H$, $R^5 = R^6 = OEt$,
$A = CH$, $B = S$, $Y = C = O$
Mp: 210–212° C.
Recrystallization Solvent: Chloroform-n-hexane Example 7
Structure:
$R^1 = 6\text{-OMe}$, $R^2 = R^3 = R^4 = H$, $R^5 = R^6 = OEt$,
$A = CH$, $B = S$, $Y = C = O$
Mp: 175–177° C.
Recrystallization Solvent: Chroloform-n-hexane Example 8
Structure:
$R^1 = 6\text{-OEt}$, $R^2 = R^3 = R^4 = H$, $R^5 = R^6 = OEt$,
$A = CH$, $B = S$, $Y = C = O$
Mp: 204.5–206.5° C.
Recrystallization Solvent: Chloroform-n-hexane Example 9
Structure:
$R^1 = 6\text{-F}$, $R^2 = R^3 = R^4 = H$, $R^5 = R^6 = OEt$, $A = CH$, $B = S$, $Y = C = O$
Mp: 210.5–212.5° C.
Recrystallization Solvent: Chloroform-n-hexane Example 10
Structure:
$R^1 = 6\text{-Cl}$, $R^2 = R^3 = R^4 = H$, $R^5 = R^6 = OEt$,
$A = CH$, $B = S$, $Y = C = O$
Mp: 227–229° C.
Recrystallization Solvent: Chloroform-n-hexane Example 11
Structure:
$R^1 = 6\text{-Br}$, $R^2 = R^3 = R^4 = H$, $R^5 = R^6 = OEt$, TABLE 1-continued

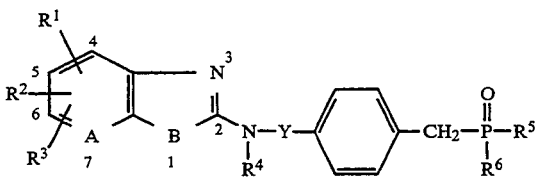

OEt: ethoxy group, Me: methyl group,
OMe: methoxy group, Ph: phenyl group

A = CH, B = S, Y = C = O
Mp: 228–229.5° C.
Recrystallization Solvent: Ethanol-n-hexane
Example 12
Structure:
$R^1 = 6\text{-}NO_2$, $R^2 = R^3 = R^4 = H$, $R^5 = R^6 = OEt$,
A = CH, B = S, Y = C = O
Mp: 249–251° C.
Recrystallization Solvent: Ethyl acetate-n-hexane
Example 13
Structure:
$R^1 = 4\text{-}OMe$, $R^2 = 6\text{-}OMe$, $R^3 = R^4 = H$,
$R^5 = R^6 = OEt$, A = CH, B = S, Y = C = O
Mp: 210–211° C.
Recrystallization Solvent: Dichloromethane-n-hexane
Example 14
Structure:
$R^1 = 5\text{-}Me$, $R^2 = 6\text{-}Me$, $R^3 = R^4 = H$,
$R^5 = R^6 = OEt$, A = CH, B = S, Y = C = O
Mp: 219–221° C.
Recrystallization Solvent: Ethanol-n-hexane
Example 15
Structure:
$R^1 = 5\text{-}Cl$, $R^2 = 6\text{-}OMe$, $R^3 = R^4 = H$,
$R^5 = R^6 = OEt$, A = CH, B = S, Y = C = O
Mp: 209–212° C.
Recrystallization Solvent: Dichloromethane-n-hexane
Example 16
Structure:
$R^1 = 4\text{-}COMe$, $R^2 = 6\text{-}OMe$, $R^3 = 7\text{-}OMe$, $R^4 = H$,
$R^5 = R^6 = OEt$, A = C, B = S, Y = C = O
Mp: 184–187° C.
Recrystallization Solvent: Chloroform-n-hexane
Example 17
Structure:
$R^1 = 4\text{-}OMe$, $R^2 = R^3 = H$, $R^4 = Me$, $R^5 = R^6 = OEt$,
A = CH, B = S, Y = C = O
Mp: 168–169° C.
Recrystallization Solvent: Dichloromethane-n-hexane
Example 18
Structure:
$R^1 = 4\text{-}OMe$, $R^2 = R^3 = H$, $R^4 = Ph\text{-}CH_2\text{-}$,
$R^5 = R^6 = OEt$, A = CH, B = S, Y = C = O
Mp: 116–119° C.
Recrystallization Solvent: Dichloromethane-n-hexane
Example 19
Structure:
$R^1 = 4\text{-}OMe$, $R^2 = R^3 = R^4 = H$, $R^5 = R^6 = OEt$,
A = CH, B = S, Y = $SO_2$
Mp: 200–204° C.
Recrystallization Solvent: Dichloromethane-n-hexane
Example 20
Structure:
$R^1 = 4\text{-}OMe$, $R^2 = R^3 = R^4 = H$, $R^5 = R^6 = OMe$,
A = CH, B = S, Y = C = O
Mp: 162.5–164.5° C.
Recrystallization Solvent: Ethyl acetate
Example 21
Structure:
$R^1 = R^2 = R^3 = R^4 = H$, $R^5 = R^6 = OEt$,
A = N, B = S, Y = C = O
Mp: 206–208° C.
Recrystallization Solvent: Methanol-n-hexane
Example 22
Structure:
$R^1 = R^2 = R^3 = H$, $R^4 = Me$,
$R^5 = R^6 = OEt$, A = N, B = S, Y = C = O
Mp: 133–135° C.

TABLE 1-continued

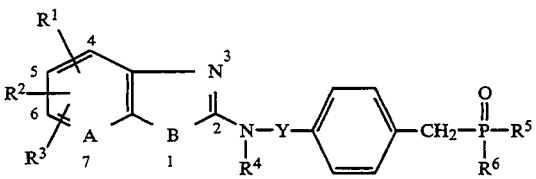

OEt: ethoxy group, Me: methyl group,
OMe: methoxy group, Ph: phenyl group

Recrystallization Solvent: Dichloromethane-n-hexane
Example 23
Structure:
$R^1 = R^2 = R^3 = H$, $R^4 = Ph\text{-}CH_2\text{-}$, $R^5 = R^6 = OEt$,
A = N, B = S, Y = C = O
Mp: 137–139° C.
Recrystallization Solvent: Dichloromethane-n-hexane
Example 24
Structure:
$R^1 = R^2 = R^3 = R^4 = H$, $R^5 = R^6 = OEt$, A = CH,
B = NH, Y = C = O
Mp: 173.5–175.5° C.
Recrystallization Solvent: Ethyl acetate-n-hexane
Example 25
Structure:
$R^1 = R^2 = R^3 = R^4 = H$, $R^5 = R^6 = OEt$, A = CH,
B = N—Me, Y = C = O
Mp: 188–190° C.
Recrystallization Solvent: Ethyl acetate-n-hexane
Example 26
Structure:
$R^1 = R^2 = R^3 = R^4 = H$, $R^5 = R^6 = OEt$, A = CH,
B = N—$CH_2Ph$, Y = C = O
Mp: 112–113° C.
Recrystallization Solvent: Ethyl acetate-n-hexane

TABLE 2

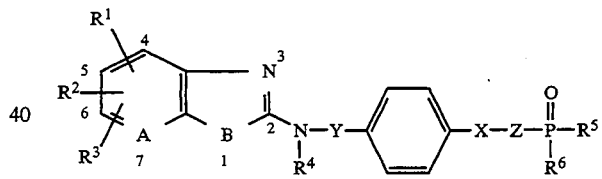

OEt: ethoxy group, Me: methyl group,
OMe: methoxy group, Ph: phenyl group

Example 27
Structure:
$R^1 = 4\text{-}OMe$, $R^2 = R^3 = R^4 = H$,
$R^5 = R^6 = -OCH(CH_3)_2$, A = CH, B = S,
Y = C = O, X = Single bond, Z = $-CH_2-$
Mp: 206.5–207.5° C.
Recrystallization Solvent: Ethyl acetate-n-hexane
Example 28
Structure:
$R^1 = 4\text{-}OMe$, $R^2 = R^3 = R^4 = H$,
$R^5 = R^6 = -O\text{-}n\text{-}C_4H_9$, A = CH, B = S, Y = C = O
X = Single bond, Z = $-CH_2-$
Mp: 167–168.5° C.
Recrystallization Solvent: Ethanol-n-hexane
Example 29
Structure:
$R^1 = 4\text{-}OMe$, $R^2 = R^3 = R^4 = H$, $R^5 = OMe$,
$R^6 = OEt$, A = CH, B = S, Y = C = O, X = Single bond,
Z = $-CH_2-$
Mp: 166–168° C.
Recrystallization Solvent: Ethyl acetate-n-hexane
Example 30
Structure:
$R^1 = 4\text{-}OMe$, $R^2 = R^3 = R^4 = H$, $R^5 = OEt$,
$R^6 = -OCH(CH_3)_2$, A = CH, B = S, Y = C = O,
X = Single bond, Z = $-CH_2-$
Mp: 155~157° C.
Recrystallization Solvent: Ethanol-n-hexane TABLE 2-continued

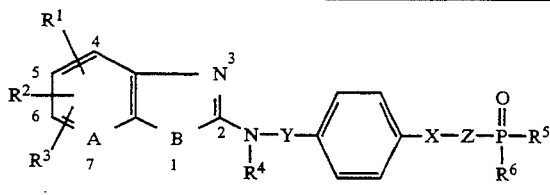

OEt: ethoxy group, Me: methyl group,
OMe: methoxy group, Ph: phenyl group

Example 31
Structure:
$R^1 = 4\text{-OMe}$, $R^2 = R^3 = R^4 = H$, $R^5 = Ph$,
$R^6 = OEt$, $A = CH$, $B = S$, $Y = C = O$
$X$ = Single bond, $Z = -CH_2-$
Mp: 101~104° C.
Recrystallization Solvent: Ethyl acetate-n-hexane
Example 32
Structure:
$R^1 = 6\text{-}CF_3$, $R^2 = R^3 = R^4 = H$, $R^5 = R^6 = OEt$,
$A = CH$, $B = S$, $Y = C = O$, $X$ = Single bond, $Z = -CH_2-$
Mp: 223-224.5° C.
Recrystallization Solvent: Dichloromethane-n-hexane
Example 33
Structure:
$R^1 = 4\text{-COPh}$, $R^2 = 6\text{-Cl}$, $R^3 = R^4 = H$,
$R^5 = R^6 = OEt$, $A = CH$, $B = S$, $Y = C = O$,
$X$ = Single bond, $Z = -CH_2-$
Mp: 233-234° C. (dec.)
Recrystallization Solvent: Chloroform-n-hexane
Example 34
Structure:
$R^1 = 4\text{-COMe}$, $R^2 = 6\text{-Br}$, $R^3 = R^4 = H$,
$R^5 = R^6 = OEt$, $A = CH$, $B = S$, $Y = C = O$,
$X$ = Single bond, $Z = -CH_2-$
Mp: 219~220° C. (dec.)
Recrystallization Solvent: Dichloromethane-n-hexane
Example 35
Structure:
$R^1 = 6\text{-COOEt}$, $R^2 = R^3 = R^4 = H$, $R^5 = R^6 = OEt$,
$A = CH$, $B = S$, $Y = C = O$, $X$ = Single bond, $Z = -CH_2-$
Mp: 225~226.5° C.
Recrystallization Solvent: Chloroform-n-hexane
Example 36
Structure:
$R^1 = 6\text{-SMe}$, $R^2 = R^3 = R^4 = H$, $R^5 = R^6 = OEt$,
$A = CH$, $B = S$, $Y = C = O$, $X$ = Single bond, $Z = -CH_2-$
Mp: 179-180° C.
Recrystallization Solvent: Dichloromethane-n-hexane
Example 37
Structure:
$R^1 = 6\text{-}OCH_2Ph$, $R^2 = R^3 = R^4 = H$, $R^5 = R^6 = OEt$,
$A = CH$, $B = S$, $Y = C = O$, $X$ = Single bond, $Z = -CH_2-$
Mp: 182-183° C.
Recrystallization Solvent: Chloroform-n-hexane
Example 38
Structure:
$R^1 = 6\text{-}CONH_2$, $R^2 = R^3 = R^4 = H$, $R^5 = R^6 = OEt$,
$A = CH$, $B = S$, $Y = C = O$, $X$ = Single bond, $Z = -CH_2-$
Mp: 257-258.5° C.
Recrystallization Solvent: Chloroform-methanol
Example 39
Structure:
$R^1 = 4\text{-OMe}$, $R^2 = R^3 = R^4 = H$, $R^5 = R^6 = OPh$,
$A = CH$, $B = S$, $Y = C = O$, $X = O$, $Z$ = Single bond
$^1$H-NMR($\delta$:ppm)[CDCl$_3$]:
3.55(s, 3H), 6.73(d, 1H, J=7.9Hz),
7.1-7.5(m, 12H), 7.9-8.4(m, 4H),
12.0(br. s, 1H)
MS(EI)m/z:
532(M$^+$), 353(M-C$_8$H$_7$N$_2$OS, base)
Example 40
Structure:
$R^1 = 5\text{-Cl}$, $R^2 = R^3 = R^4 = H$, $R^5 = R^6 = OEt$,
$A = CH$, $B = O$, $Y = C = O$, $X$ = Single bond, $Z = -CH_2-$
Mp: 190.5~192.0° C.
Recrystallization Solvent: Ethyl acetate
Example 41

TABLE 2-continued

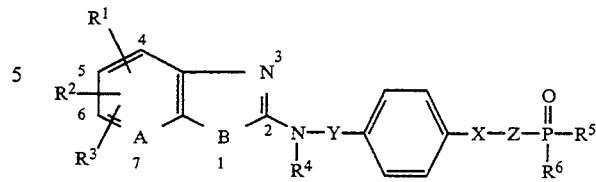

OEt: ethoxy group, Me: methyl group,
OMe: methoxy group, Ph: phenyl group

Structure:
$R^1 = 6\text{-}OCH_2-COOEt$, $R^2 = R^3 = R^4 = H$,
$R^5 = R^6 = OEt$,
$A = CH$, $B = S$, $Y = C = O$, $X$ = Single bond, $Z = -CH_2-$
Mp: 187.5-188.5° C.
Recrystallization Solvent: Chloroform-n-hexane
Example 42
Structure:
$R^1 = 4\text{-OMe}$, $R^2 = R^3 = R^4 = H$, $R^5 = R^6 = OEt$, $A = CH$, $B = S$, $Y = C = O$, $X$ = Single bond, $Z = -\underset{CH_2Ph}{CH-}$ Mp: 74-76° C.
Recrystallization Solvent: Chloroform-n-hexane
Example 43
Structure:
$R^1 = 4\text{-OMe}$, $R^2 = R^3 = R^4 = H$, $R^5 = R^6 = OEt$, $A = CH$, $B = S$, $Y = C = O$, $X$ = Single bond, $Z = -\underset{CH_3}{CH-}$ Mp: 85-87° C.
Recrystallization Solvent: Ethanol-n-hexane
Example 44
Structure:
$R^1 = 4\text{-Ph}$, $R^2 = 6\text{-Br}$, $R^3 = R^4 = H$,
$R^5 = R^6 = OEt$, $A = CH$, $B = S$, $Y = C = O$,
$X$ = Single bond, $Z = -CH_2-$
Mp: 208~209° C.
Recrystallization Solvent: Chloroform-n-hexane
Example 45
Structure:
$R^1 = 4\text{-OMe}$, $R^2 = R^3 = R^4 = H$, $R^5 = OEt$,
$R^6 = OCH_2Ph$, $A = CH$, $B = S$, $Y = C = O$,
$X$ = Single bond, $Z = -CH_2-$
Mp: 140-143° C.
Recrystallization Solvent: Ethyl acetate-n-hexane
Example 46
Structure:
$R^1 = 4\text{-OMe}$, $R^2 = R^3 = R^4 = H$, $R^5 = OH$, $R^6 = OEt$,
$A = CH$, $B = S$, $Y = C = O$, $X$ = Single bond, $Z = -CH_2-$
Mp: 255-256.5° C. (dec.)
Example 47
Structure:
$R^1 = 4\text{-OMe}$, $R^2 = R^3 = R^4 = H$, $R^5 = R^6 = OEt$,
$A = CH$, $B = S$, $Y = C = O$, $X = O$, $Z = -CH_2CH_2-$
Mp: 150-153° C.
Recrystallization Solvent: Dichloromethane-n-hexane
Example 48
Structure:
$R^1 = 4\text{-OMe}$, $R^2 = R^3 = R^4 = H$, $R^5 = R^6 = OEt$,
$A = CH$, $B = S$, $Y = C = O$, $X = O$, $Z = -CH_2CH_2CH_2-$
Mp: 168~170.5° C.
Recrystallization Solvent: Ethanol-n-hexane

FORMULATION EXAMPLE 1

Manufacture of tablets using the compound obtained in Example 3 as an active ingredient, tablets (1000 tablets) each containing 250 mg of the active ingredient were manufactured according to the following formula.

| Ingredient | Amount (g) |
| --- | --- |
| Compound of Example 3 | 250 |
| Lactose (JP) | 33.5 |
| Corn starch (JP) | 16.5 |
| Carboxymethylcellulose calcium (JP) | 12.5 |
| Methylcellulose (JP) | 6.0 |
| Magnesium stearate (JP) | 1.5 |
| Total | 320.0 |

According to the above formula, the compound of Example 3, lactose, corn starch and carboxymethyl cellulose calcium were well blended and granulated using an aqueous solution of methyl cellulose. The granulation was passed through a 24-mesh sieve and the granules under the sieve were mixed with magnesium stearate and compression-molded.

FORMULATION EXAMPLE 2

Manufacture of Capsules

Using the compound obtained in Example 5 as an active ingredient, hard gelatin capsules (1000 units) each containing 250 mg of the active ingredient were manufactured according to the following formula.

| Ingredient | Amount (g) |
| --- | --- |
| Compound of Example 5 | 250 |
| Crystalline cellulose (JP) | 30 |
| Corn starch (JP) | 17 |
| Talc (JP) | 2 |
| Magnesium stearate (JP) | 1 |
| Total | 300 |

Thus, according to the above formula, the respective ingredients were finely divided and the powders obtained were blended to give a homogeneous composition. This composition was filled into proper-sized gelatin capsule shells for oral administration to provide the objective capsules.

FORMULATION EXAMPLE 3

Manufacture of Granules

Using the compound obtained in Example 13 as an active ingredient, granules (1000 g) containing 500 mg of the active ingredient in each gram were manufactured according to the following formula.

| Ingrdient | Amount (g) |
| --- | --- |
| Compound of Example 13 | 500 |
| Crystalline cellulose (JP) | 100 |
| Corn starch (JP) | 250 |
| Lactose (JP) | 100 |
| Carboxymethylcellulose calcium (JP) | 40 |
| Hydroxypropylmethylcellulose (JP) | 10 |
| Total | 1000 |

Thus, according to the above formula, the compound of Example 13, lactose, corn starch, crystalline cellulose and carboxymethylcellulose calcium were thoroughly blended and kneaded with an aqueous solution of hydroxypropylcellulose. The resultant composition was granulated using an extrusion granulator and dried at 50° C. for 2 hours to provide the objective granules.

PHARMACOLOGICAL TEST EXAMPLE 1

Hypolipidemic Effect in Rats with Triton WR1339-Induced Hyperlipidemia

An experiment for assaying hypolipidemic activity in rats with Triton WR1339-induced hyperlipidemia was performed according to the method of Kuroda et al. [Biochem. Biophys. Acta., 489, 119 (1977)], as follows.

Thus, using 6-7-week-old male Wistar rats in groups of 6 (test groups), a solution of 300 mg/kg Triton in physiological saline was administered into the tail vein and, at the same time, 100 mg/kg of the test compound suspended in 5% gum arabic solution was administered orally.

As a control group, a group of 6 rats given Triton were orally dosed with 5% gum arabic solution.

Twenty-four hours after administration of Triton, blood was withdrawn from the abdominal aorta and the plasma total cholesterol and triglyceride were determined using Cholesterol C-Test Wako and Triglyceride G-Test Wako (both available from Wako Pure Chemical Industries, Ltd.), respectively.

Using the measured values in the control group as references, the rates of decrease (%) in plasma total cholesterol and triglyceride in the test group were calculated by means of the following equation.

$$\text{Rate of decrease (\%)} = \frac{(\text{Control group value}) - (\text{Test group value})}{(\text{Control group value})} \times 100$$

The test rats were deprived of food before Triton administration through completion of blood sampling but allowed free access to drinking water. The rates of decrease in total cholesterol are shown in Table 3 and those in triglyceride are shown in Table 4.

TABLE 3

| Test compound (Example No.) | Rate of decrease in total cholesterol (%) |
| --- | --- |
| 1 | 40 |
| 3 | 56 |
| 13 | 70 |
| 26 | 43 |
| 27 | 42 |
| 29 | 47 |
| 30 | 79 |
| 31 | 69 |
| 34 | 71 |
| 42 | 45 |
| 43 | 45 |
| 45 | 62 |

TABLE 4

| Test compound (Example No.) | Rate of decrease in triglyceride (%) |
| --- | --- |
| 1 | 62 |
| 2 | 44 |
| 3 | 83 |
| 4 | 47 |
| 10 | 40 |
| 11 | 44 |
| 13 | 94 |
| 20 | 48 |
| 25 | 54 |
| 26 | 63 |
| 27 | 81 |
| 29 | 87 |
| 30 | 95 |
| 31 | 92 |
| 32 | 47 |

TABLE 4-continued

| Test compound (Example No.) | Rate of decrease in triglyceride (%) |
|---|---|
| 34 | 97 |
| 42 | 81 |
| 43 | 80 |
| 45 | 91 |

It is apparent from Tables 3 and 4 that all species of the compound of the invention have excellent hypolipidemic activity.

PHARMACOLOGICAL TEST EXAMPLE 2

Hypoglycemic Effect in Rats with Streptozotocin-Induced Diabetes

The rat model of streptozotocin-induced diabetes was constructed according to Doi's method [Folia Endocrinologica Japonica, 51 (3), 129 (1975)] as below and the hypoglycemic activity of the compound of the invention was assayed in the model by the following procedure.

Thus, using 5-week-old male Wistar rats in groups of 7 (test groups), 100 mg/kg of streptozotocin dissolved in 0.01M citrate buffer (pH 4.5) was administered into the tail vein and on day 6 after this administration, a suspension of 30 mg/kg of the compound obtained in Example 3 in 5% gum arabic solution was orally administered.

As a control group, a group of 6 rats given streptozotocin were orally dosed with 5% gum arabic solution.

Four hours after administration of the test compound or 5% gum arabic solution, blood was withdrawn from the abdominal aorta and the plasma glucose was determined using Glucose C II-Test Wako (Wako Pure Chemical Industries, Ltd.).

The results in terms of mean±SD are shown below in Table 5.

TABLE 5

| | Plasma glucose level (mg/dl) |
|---|---|
| Control group | 588 ± 69 |
| Test group | 495 ± 53** |

**: $P < 0.01$ [Dunnet's test]

It is apparent from the above table that the plasma glucose level in the test group was significantly depressed as compared with the control group, indicating that the compound of the invention has excellent hypoglycemic activity.

We claim:

1. A phosphonic diester derivative of the general formula

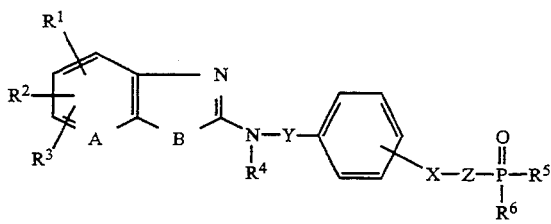

wherein $R^1$, $R^2$ and $R^3$ are the same or different and each represents a hydrogen atom, a lower alkyl group, a phenyl group, a lower alkoxy group, a halogen-substituted lower alkyl group, a halogen-substituted lower alkoxy group, a lower alkanoyl group, a benzoyl group, a (lower)alkoxycarbonyl group, a nitro group, a halogen atom, a (lower)alkylthio group, a phenyl(lower)alkoxy group, a carbamoyl group or a (lower)alkoxycarbonyl(lower)alkoxy group; $R^4$ represents a hydrogen atom, a lower alkyl group or a phenyl(lower)alkyl group; $R^5$ and $R^6$ are the same or different and each represents a lower alkoxy group, a phenyl group, a phenoxy group, a phenyl(lower)alkoxy group or a hydroxyl group; A represents a carbon atom or a nitrogen atom; B represents a group of the formula $=NR^7$, wherein $R^7$ represents a hydrogen atom, a lower alkyl group or a phenyl(lower)alkyl group, an oxygen atom or a sulfur atom; Y represents a group of the formula $C=O$ or a group of $SO_2$; X represents an oxygen atom or a bond; Z represents a lower alkylene group optionally having a lower alkyl or phenyl(lower)alkyl group as a substituent or a bond; provided, however, that X and Z do not concurrently represent bonds.

2. The phosphonic diester derivative of claim 1 which is represented by the general formula

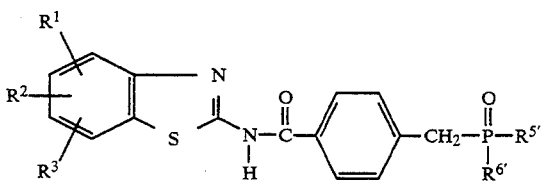

wherein $R^1$, $R^2$ and $R^3$ are the same or different and each represents a hydrogen atom, a lower alkyl group, a phenyl group, a lower alkoxy group, a halogen-substituted lower alkyl group, a halogen-substituted lower alkoxy group, a lower alkanoyl group, a benzoyl group, a (lower)alkoxycarbonyl group, a nitro group, a halogen atom, a (lower)alkylthio group, a phenyl(lower)alkoxy group, a carbamoyl group or a (lower)alkoxycarbonyl(lower)alkoxy group; $R^{5'}$ and $R^{6'}$ are the same or different and each represents a lower alkoxy group, a phenyl group or a phenyl(lower)alkoxy group.

3. The phosphonic diester derivative of claim 2 wherein $R^1$, $R^2$ and $R^3$ are groups selected from the group consisting of a hydrogen atom, a lower alkoxy group, a lower alkanoyl group and a halogen atom.

4. The phosphonic diester derivative of claim 3 which may be represented by the general formula

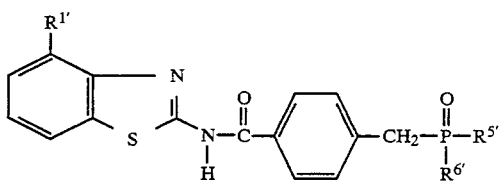

wherein $R^{1'}$ represents a lower alkoxy group, $R^{5'}$ and $R^{6'}$ are the same or different and each represents a lower alkoxy group, a phenyl group or a phenyl(lower)alkoxy group.

5. The phosphonic diester derivative of claim 3 which is a compound selected from the group consisting of (1) Diethyl 4-[(4-methoxybenzothiazol-2-yl)carbamoyl]benzylphosphonate, (2) Diethyl 4-[(4,6-dimethoxybenzothiazol-2-yl)-carbamoyl]benzylphosphonate, (3) Diethyl 4-[(4-acetyl-6-bromobenzothiazol-2-yl)carbamoyl]benzylphosphonate, and (4) Diethyl 4-[(4-chlorobenzothiazol-2-yl)carbamoyl]benzylphosphonate.

6. The phosphonic diester derivative of claim 5 which is diethyl 4-[(4-methoxybenzothiazol-2-yl)-carbamoyl]benzylphosphonate.

7. An antihyperlipidemic composition comprising the phosphonic diester derivative claimed in any of claims 1 through 6 as an active ingredient.

8. An antidiabetic composition comprising the phosphonic diester derivative claimed in any of claims 1 through 6 as an active ingredient.

9. A method of treating hyperlipidemia characterized by administering to a patient a pharmacologically effective amount of the antihyperlipidemic composition claimed in claim 7.

10. A method of treating diabetes characterized by administering a pharmacologically effective amount of the antidiabetic composition claimed in claim 8.

* * * * *